(12) United States Patent
Shibata et al.

(10) Patent No.: US 11,022,277 B2
(45) Date of Patent: Jun. 1, 2021

(54) WAVELENGTH CONVERTER AND LIGHTING APPARATUS

(71) Applicant: PANASONIC INTELLECTUAL PROPERTY MANAGEMENT CO., LTD., Osaka (JP)

(72) Inventors: Yudai Shibata, Hyogo (JP); Shintaro Hayashi, Hyogo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 16/822,745

(22) Filed: Mar. 18, 2020

(65) Prior Publication Data

US 2020/0309349 A1 Oct. 1, 2020

(30) Foreign Application Priority Data

Mar. 27, 2019 (JP) .............................. JP2019-061992

(51) Int. Cl.

| | |
|---|---|
| F21V 9/00 | (2018.01) |
| F21V 9/32 | (2018.01) |
| F21V 5/04 | (2006.01) |
| F21V 29/502 | (2015.01) |
| F21V 29/74 | (2015.01) |
| H01S 5/323 | (2006.01) |
| H01S 5/02251 | (2021.01) |
| F21Y 115/30 | (2016.01) |

(52) U.S. Cl.
CPC ............... *F21V 9/32* (2018.02); *F21V 5/045* (2013.01); *F21V 29/502* (2015.01); *F21V 29/74* (2015.01); *H01S 5/02251* (2021.01); *H01S 5/32341* (2013.01); *F21Y 2115/30* (2016.08)

(58) Field of Classification Search
CPC ............ H01S 5/02284; H01S 5/02288; G02B 19/0052; F21V 5/045; F21V 9/30; F21V 9/32; F21Y 2115/30
See application file for complete search history.

(56) References Cited

U.S. PATENT DOCUMENTS

| | | | |
|---|---|---|---|
| 7,630,032 B2 | 12/2009 | Kirita et al. | |
| 2006/0050198 A1 | 3/2006 | Kirita et al. | |
| 2013/0105850 A1* | 5/2013 | Komatsu | F21S 41/143 257/98 |
| 2016/0077415 A1 | 3/2016 | Motoya et al. | |
| 2018/0347785 A1* | 12/2018 | Kawaguchi | F21V 9/30 |

FOREIGN PATENT DOCUMENTS

| | | |
|---|---|---|
| JP | 2006-072249 | 3/2006 |
| JP | 2015-001709 | 1/2015 |
| JP | 2016-058638 | 4/2016 |
| JP | 2017-173370 | 9/2017 |

* cited by examiner

*Primary Examiner* — Y M. Lee
(74) *Attorney, Agent, or Firm* — Greenblum & Bernstein, P.L.C.

(57) ABSTRACT

A wavelength converter includes a base, a wavelength converting component that converts a wavelength of at least part of excitation light to emit converted light, and an optical filter disposed between the base and the wavelength converting component. The optical filter transmits or absorbs, out of the converted light including a wavelength range of from approximately 470 nm to approximately 750 nm, converted light of a predetermined wavelength included in the wavelength range.

16 Claims, 8 Drawing Sheets

WAVELENGTH CONVERTER AND LIGHTING APPARATUS

CROSS REFERENCE TO RELATED APPLICATION

This application claims the benefit of priority of Japanese Patent Application Number 2019-061992, filed on Mar. 27, 2019, the entire content of which is hereby incorporated by reference.

TECHNICAL FIELD

The present disclosure relates to a wavelength converter and to a lighting apparatus using the wavelength converter.

BACKGROUND ART

For example, Japanese Unexamined Patent Application Publication No. 2015-1709 discloses a light source apparatus that includes a semiconductor laser, a wavelength converting component that wavelength-converts laser light which is the light from the semiconductor laser, and a first filter that is disposed between the semiconductor laser and the wavelength converting component, and transmits the light from the semiconductor laser while reflecting the light that was wavelength-converted by the wavelength converting component.

SUMMARY

In the above-described conventional technique, when the wavelength converting component emits the light resulting from the wavelength conversion of laser light, the first filter reflects the wavelength-converted light. However, for example, when the light converted by the wavelength converting component is used to illuminate the surroundings, there are cases where illumination with light having sufficient color rendering property is not possible.

In view of this, the present disclosure provides a wavelength converter and a lighting apparatus that are capable of improving the color rendering property of light emitted from the wavelength converter.

A wavelength converter according to an aspect of the present disclosure includes a base, a wavelength converting component that converts a wavelength of at least part of excitation light to emit converted light, and an optical filter disposed between the base and the wavelength converting component, wherein the optical filter transmits or absorbs, out of the converted light which includes a wavelength range of from approximately 470 nm to approximately 750 nm, converted light of a predetermined wavelength included in the wavelength range.

Furthermore, a lighting apparatus according to an aspect of the present disclosure includes the above-described wavelength converter, and an excitation light source that emits the excitation light.

A wavelength converter and a lighting apparatus according to the present disclosure are capable of improving the color rendering property of light emitted from the wavelength converter.

BRIEF DESCRIPTION OF THE DRAWINGS

The figures depict one or more implementations in accordance with the present teaching, by way of examples only, not by way of limitations. In the figures, like reference numerals refer to the same or similar elements.

DETAILED DESCRIPTION

Hereinafter, exemplary embodiments of the present disclosure will be described with reference to the drawings. It should be noted that each of the subsequently-described exemplary embodiments shows a specific example of the present disclosure. The numerical values, shapes, materials, structural elements, the arrangement and connection of the structural elements, as well as procedural steps and the sequence of the steps, etc., shown in the following exemplary embodiments are mere examples, and are not intended to limit the scope of the present disclosure. Therefore, among the structural elements in the following exemplary embodiments, elements not recited in any one of the independent claims which indicate the broadest concepts of the present disclosure are described as arbitrary structural elements.

The respective figures are schematic diagrams and are not necessarily precise illustrations. Therefore, for example, the scales, etc. in the respective figures are not necessarily uniform. Furthermore, in the drawings, substantially identical components are assigned the same reference signs, and overlapping description is omitted or simplified.

A wavelength converter and a lighting apparatus according to the subsequent exemplary embodiments will be described.

Embodiment

Configuration

Lighting Apparatus 1

Figure 1A:
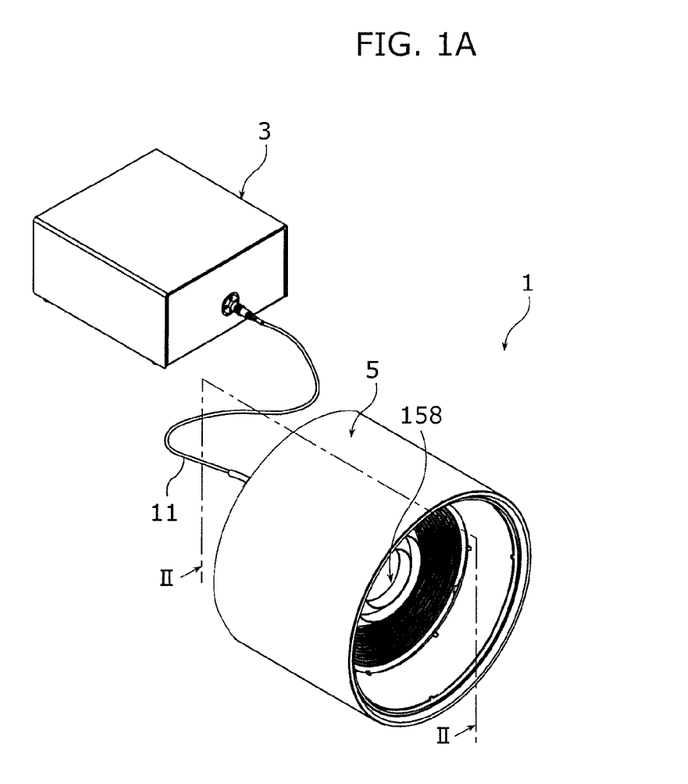
FIG. 1A is a perspective view of a lighting apparatus according to an embodiment.
Figure 2A:
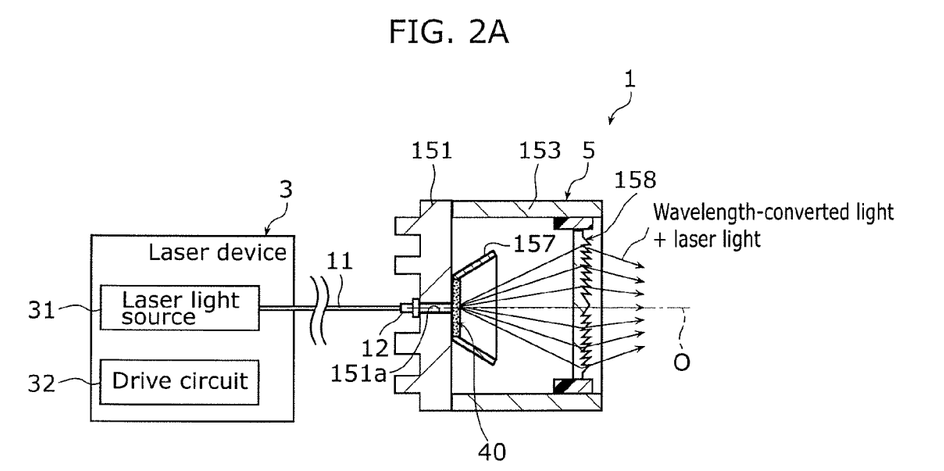
FIG. 2A is a schematic diagram illustrating an example of structural elements according to the embodiment in the lighting apparatus in FIG. 1A, and shows a cross-sectional view of a luminaire, etc., taken along line II-II in FIG. 1A.

FIG. 1A is a perspective view of lighting apparatus 1 according to an embodiment. FIG. 2A is a schematic diagram illustrating an example of structural elements of lighting apparatus 1 according to the embodiment, and shows a cross-sectional view of luminaire 5, etc., taken along line II-II in FIG. 1A.

As illustrated in FIG. 1A and FIG. 2A, lighting apparatus 1 is a transmission type lighting apparatus that uses laser light, and includes laser device 3, optical fiber 11, ferrule 12, and luminaire 5. Luminaire 5 includes therein wavelength converter 40. Lighting apparatus 1 is used in, for example, a downlight, a spotlight, etc. Here, transmission type lighting apparatus 1 which uses laser light is an apparatus in which the back face of wavelength converter 40 is irradiated with laser light and converted light (fluorescence) resulting from wavelength conversion is emitted from the front face of wavelength converter 40.

Laser Device 3

Laser device 3 is a device that includes one or more lasers and emits laser light. In this embodiment, laser device 3 includes one or more lasers. For example, as illustrated in FIG. 2A, laser device 3 includes laser light source 31 and drive circuit 32. Laser light is an example of excitation light.

(Laser Light Source 31)

As illustrated in FIG. 2A, laser light source 31 emits laser light. Laser light source 31 causes the laser light to enter an incidence face which is one end face of optical fiber 11. It should be noted that, in this embodiment, a single laser light source 31 may be used or a plurality of laser light sources 31 may be used. Laser light source 31 is an example of an excitation light source.

Laser light source 31 may use a semiconductor laser, or may use, for example, an InGaN-based laser diode or an AlInGaN-based laser diode. Laser light source 31 may use, for example, a light emitting diode (LED) as long as the light emitted is capable of exciting subsequently-described wavelength converting component 43 of wavelength converter 40.

It should be noted that the output of laser light emitted by laser light source 31 is controlled by drive circuit 32. In this embodiment, the laser light emitted by laser light source 31 is light of a predetermined wavelength included in a wavelength band ranging from violet to blue. Laser light that is violet, blue, etc., is of a color that can be objectively recognized as laser light that is purple, blue, etc.

(Drive Circuit 32)

Drive circuit 32 is electrically connected to a power system using a power line, or the like, and supplies power to laser light source 31. Furthermore, drive circuit 32 performs drive control of the output of laser light source 31 so that laser light source 31 emits a predetermined laser light.

Furthermore, drive circuit 32 has a function of adjusting the laser light emitted by each laser light source 31. Drive circuit 32 may be an oscillator that drives laser light source 31 based on pulse signals.

Figure 3A:
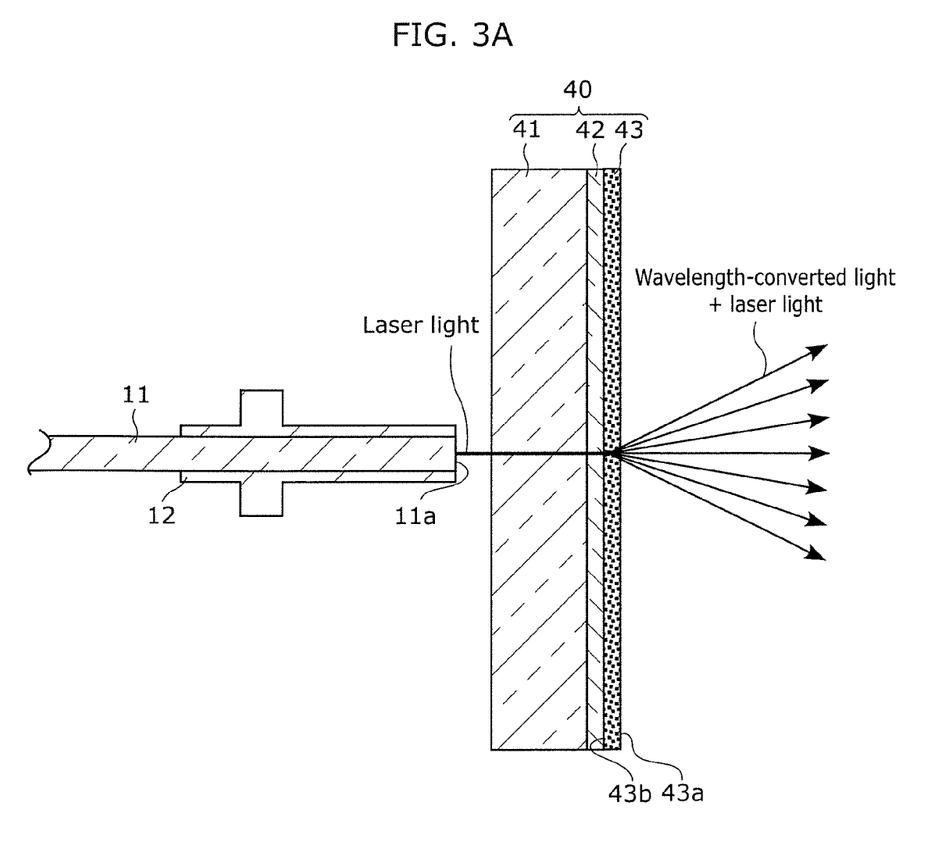
FIG. 3A is an enlarged partial sectional view of an example of an optical fiber and a wavelength converter of the lighting apparatus according to the embodiment in FIG. 1A.

Next, the configuration of optical fiber 11, etc., will be described with reference to FIG. 3A. FIG. 3A is an enlarged partial sectional view of an example of optical fiber 11 and wavelength converter 40 of lighting apparatus 1 according to the embodiment.

Optical Fiber 11

As illustrated in FIG. 2A and FIG. 3A, optical fiber 11 is a transmission component having a two-layered structure consisting of a core that has a high refractive index and a cladding layer that surrounds the core and has a lower refractive index than the core, and is formed using a material such as silica glass or plastic, for example. Optical fiber 11 transmits laser light emitted by laser light source 31. In this embodiment, optical fiber 11 transmits the laser light emitted by a corresponding laser from among the one or more laser light sources 31. The laser light emitted by the one or more laser light sources 31 enters one end of optical fiber 11 and exits from the other end of optical fiber 11.

It should be noted that, here, the one end of optical fiber 11 is also referred to as the upstream of an optical path for transmitting laser light, and the other end is the downstream of the optical path.

As illustrated in FIG. 3A, optical fiber 11 includes emission face 11a from which the guided laser light is emitted. Emission face 11a is the other end of optical fiber 11. Emission face 11a faces wavelength converter 40 via ferrule 12 in FIG. 2A. Emission face 11a is substantially a mirror surface, that is, it is a substantially flat surface. The rough surface of emission face 11a may be formed by sanding, for example, and may be formed by cleaving optical fiber 11. It should be noted that a rough surface may be formed or a structure for reducing light loss at the end face may be formed in emission face 11a. For example, an AR coat of dielectric film, imprint processing, etc., may be given as a structure for reducing light loss. It should be noted that, from the viewpoint of laser resistance, the dielectric film may be an inorganic film.

Ferrule 12

Ferrule 12 holds the other end of optical fiber 11. Specifically, ferrule 12 holds the other end of optical fiber 11 so that the laser light emitted from emission face 11a of optical fiber 11 enters wavelength converter 40. The optical axis of ferrule 12 is a straight line that coincides with the main light emission direction, and substantially coincides with central axis O indicated by the long and short dashed line in FIG. 2A, etc.

Wavelength Converter 40

Wavelength converter 40 is a wavelength-converting body that converts laser light emitted from laser light source 31. Wavelength converter 40 is a tabular plate. In this embodiment, wavelength converter 40 includes, for example, base 41, optical filter 42, and wavelength converting component 43, and is a multilayer structure in which these elements are sequentially laminated.

Base 41 is disposed opposite ferrule 12. Base 41 is light-transmissive and is, for example, single-crystal sapphire. Laser light emitted from ferrule 12 enters base 41. Specifically, the face of base 41 which faces ferrule 12 is the incidence face of wavelength converter 40. The incidence face of base 41 is orthogonal to the optical axis of ferrule 12.

Furthermore, base 41 is secured to subsequently-described heat sink 151 of luminaire 5 in a state where base 41 is in contact with heat sink 151. Accordingly, base 41 dissipates the heat generated during wavelength conversion of laser light by wavelength converting component 43.

Optical filter 42 is laminated onto the face of base 41 which is on the side opposite to the side into which laser light enters. Specifically, optical filter 42 is disposed between base 41 and wavelength converting component 43. In this embodiment, optical filter 42 is sandwiched between base 41 and wavelength converting component 43, and is in contact with each of base 41 and wavelength converting component 43.

Optical filter 42 is an optical thin-film comprising a dielectric multilayer film. Optical filter 42 in this embodiment transmits the laser light entering from base 41, transmits or absorbs part of converted light resulting from the wavelength conversion by wavelength converting component 43, and reflects the rest of the converted light. More specifically, optical filter 42 transmits or absorbs, out of the converted light including a wavelength range of from approximately 470 nm to approximately 750 nm, converted light of a predetermined wavelength included in the wavelength range, and reflects the rest of the converted light. In this embodiment, optical filter 42 transmits or absorbs the converted light of a wavelength that is at most approximately 50 nm above and below the wavelength at which intensity of the converted light is at maximum, and reflects the rest of the converted light. Since the intensity of converted light is at maximum at approximately 550 nm, out of the converted light, optical filter 42 transmits or absorbs the converted light of a wavelength ranging from approximately 500 nm to approximately 600 nm, and reflects the rest of the converted light. In particular, optical filter 42 may transmit or absorb the converted light of a wavelength that is approximately 50 nm above and below the wavelength at which the intensity of converted light is at maximum.

Furthermore, the reflectivity of optical filter 42 for the maximum wavelength of converted light and neighboring wavelengths thereof is preferably at most approximately 50 percent. Alternatively, the rate of absorption of optical filter 42 for converted light of the predetermined wavelength is preferably at least approximately 50 percent.

Wavelength converting component 43 is laminated onto the face of optical filter 42 which is on the side opposite to the side that is laminated onto base 41. Specifically, laser light transmitted by base 41 and optical filter 42 enters wavelength converting component 43. In this embodiment, wavelength converting component 43 includes yellow phosphor, and emits yellow converted light when laser light enters.

Wavelength converting component 43 is formed in the shape of a board, for example. Wavelength converting component 43 includes phosphor (yellow phosphor in this embodiment) that emits converted light according to laser light, and the phosphor is held in a dispersed state by a binder which is a transparent material made from ceramic, silicon resin, or the like. The phosphor included in wavelength converting component 43 is, for example, an yttrium aluminum garnet (YAG)-based phosphor, a CASN-based phosphor, an SCASN-based phosphor, or a Ba, Mg, Al (BAM)-based phosphor, and can be selected as appropriate according to the type of laser light. It should be noted that the binder is not limited to ceramic or silicon resin, and other transparent material such as transparent glass, etc., may be used.

As illustrated in FIG. 3A, laser light emitted by laser light source 31 enters wavelength converting component 43, and wavelength converting component 43 wavelength-converts at least part of the laser light that has entered, and emits converted light resulting from the wavelength conversion. The converted light resulting from the wavelength conversion by wavelength converting component 43 is fluorescence. More specifically, wavelength converting component 43 has a function of wavelength-converting at least part of the laser light that has entered. In this embodiment, the face on the side of wavelength converting component 43 from which light is emitted is front face 43a of wavelength converting component 43, and the face that is in contact with optical filter 42 is back face 43b of wavelength converting component 43. In wavelength converting component 43, (i) converted light resulting from the wavelength conversion of the laser light that entered from back face 43b and (ii) the laser light that was not wavelength-converted (i.e., the laser light that passed through wavelength converting component 43 without being wavelength-converted) are emitted from front face 43a. There are instances where such converted light and laser light are collectively referred to simply as light.

It should be noted that light lost during wavelength conversion is transformed to heat. Since wavelength converting component 43 has a thermal quenching property in which wavelength conversion efficiency deteriorates with increasing temperature, heat dissipation of wavelength converting component 43 is very important. Wavelength converting component 43 is supported by heat sink 151 via base 41, etc. More specifically, wavelength converting component 43 is secured to the other end face of heat sink 151 via base 41, etc., at a position that intersects central axis O so as to be thermally connected to heat sink 151. In other words, in order to facilitate dissipation of heat generated in wavelength converting component 43, one face of wavelength converter 40 is in contact with the other end face of first heat sink 151. As illustrated in FIG. 2A, central axis O is, for example, in the case of cylindrical luminaire 5, orthogonal to the aperture plane of light emitted from luminaire 5, and is the straight line passing through the center of the aperture.

In this embodiment, in wavelength converting component 43, green to red converted light converted from part of the absorbed blue laser light from laser device 3 mixes with the blue laser light that is emitted without being absorbed by wavelength converting component 43, such that pseudo white converted light is emitted. It should be noted that, in the case where laser device 3 emits blue laser light, wavelength converting component 43 may include several types of phosphors which absorb and wavelength-convert part of the blue laser light to, for example, green to yellow converted light.

Moreover, when wavelength converting component 43 includes several types of phosphors, there are instances where there are a plurality of maximum wavelengths at which converted light intensity is at maximum. In this case, optical filter 42 may transmit or absorb the converted light of a wavelength that is approximately 50 nm above and below one maximum wavelength, or may transmit or absorb the converted light of a wavelength that is approximately 50 nm above and below each of the plurality of maximum wavelengths.

Next, luminaire 5 which controls light distribution of the light emitted from wavelength converting component 43 of wavelength converter 40 will be described.

Luminaire 5

As illustrated in FIGS. 1A and 2A, luminaire 5 is used for emitting illumination light obtained by combining the converted light resulting from the wavelength conversion of the laser light from laser device 3 that is transmitted via optical fiber 11 and the laser light that was not wavelength-converted. Luminaire 5 consists of, for example, a stainless steel fiber coupling, a glass lens, an aluminum holder, and an aluminum outer hull.

In this embodiment, luminaire 5 includes heat sink 151, exterior portion 153, reflector 157, and lens 158.

(Heat Sink 151)

As illustrated in FIG. 2A, heat sink 151 is a heat-dissipating component for dissipating heat generated in wavelength converting component 43. Heat sink 151 holds wavelength converter 40 so that it is disposed at a position that intersects central axis O.

Heat sink 151 includes a plurality of fins and insertion portion 151a.

Ferrule 12 is held in insertion portion 151a. Insertion portion 151a is a holder that holds ferrule 12 in a state where ferrule 12 is inserted therein. Furthermore, insertion portion 151a secures ferrule 12 in a predetermined orientation. In addition, insertion portion 151a is formed at a position that overlaps with central axis O.

(Exterior Portion 153)

Exterior portion 153 is connected to heat sink 151 and disposed downstream in the optical path. Specifically, exterior portion 153 is disposed further downstream in the optical path than wavelength converting component 43. Exterior portion 153 is a bottomless cylinder having openings which open to the front and back in the optical path.

(Reflector 157)

Reflector 157 reflects the converted light emitted from wavelength converting component 43 toward lens 158. Reflector 157 is bowl-shaped with a diameter that increases from wavelength converting component 43 toward lens 158. Reflector 157 is secured to the other end face of heat sink 151 so as to surround the periphery of wavelength converting component 43 and face lens 158.

(Lens 158)

Lens 158 is for example a Fresnel lens. Lens 158 is secured to exterior portion 153 so as to block an opening of exterior portion 153. Specifically, lens 158 is secured to exterior portion 153 in an orientation that is opposite to wavelength converting component 43 to enable entry of converted light emitted from wavelength converting component 43. In addition, lens 158 performs light distribution control and emission of the converted light to perform predetermined illumination.

Experiment Results

Experiment results for wavelength converter 40 according to this embodiment are described below.

Figure 4:
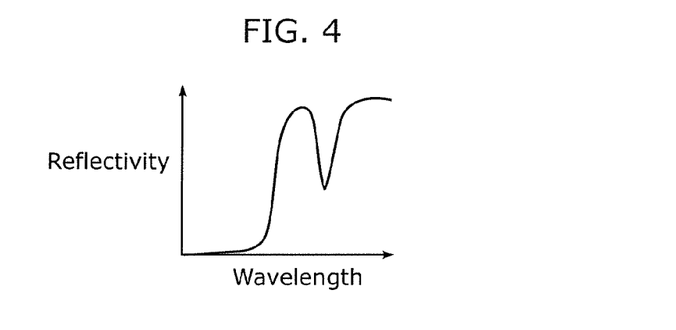
FIG. 4 is a graph illustrating an example of the wavelength and reflectivity of light of optical filters of wavelength converters of lighting apparatuses according to the embodiment and other forms.

FIG. 4 is a graph illustrating an example of the wavelength and reflectivity of light of optical filter 42 of wavelength converter 40 of lighting apparatus 1 according to this embodiment and other forms.

As illustrated in FIG. 4, in wavelength converter 40 according to this embodiment, out of the converted light resulting from the wavelength conversion of laser light by wavelength converting component 43, converted light of a predetermined wavelength is transmitted by optical filter 42. Wavelength converter 40 according to this embodiment transmits the converted light of the yellow wavelength which is included in the approximately 500 nm to approximately 650 nm wavelength range of the converted light. The reflectivity of optical filter 42 of wavelength converter 40 according to this embodiment for the maximum wavelength of converted light and the neighboring wavelengths thereof is at most approximately 50 percent.

Figure 5:
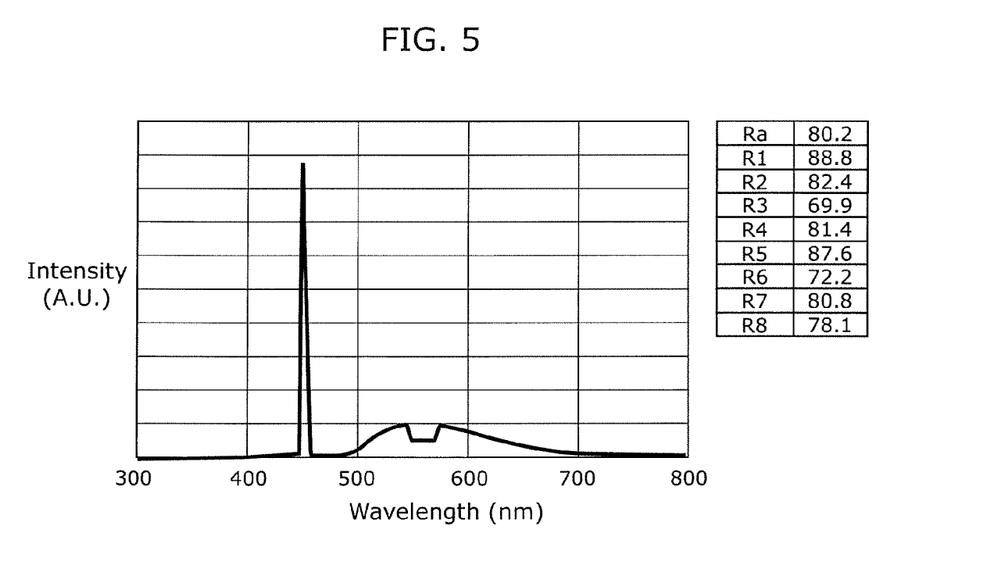
FIG. 5 illustrates a graph showing an example of intensity and wavelength of light emitted from wavelength converters of lighting apparatuses according to the embodiment and other forms, and a table showing an example of an average color rendering index.

FIG. 5 illustrates a graph showing an example of intensity and wavelength of light emitted from wavelength converter 40 of lighting apparatus 1 according to this embodiment and other forms, and a chart showing an example of an average color rendering index.

FIG. 5 illustrates the case where laser light having a peak included in a wavelength range of from approximately 430 nm to approximately 470 nm enters wavelength converter 40, when the reflectivity of optical filter 42 for the maximum wavelength of converted light and the neighboring wavelengths thereof is zero percent (when the converted light is completely transmitted). FIG. 5 illustrates the spectrum of light emitted from wavelength converter 40, when wavelength converter 40 such as that described above is used.

In FIG. 5, optical filter 42 transmits the yellow wavelength which is included in the approximately 470 nm to approximately 750 nm wavelength range of the converted light emitted from wavelength converter 40. The wavelength at which the intensity of converted light is at maximum is included in a range of from approximately 550 nm to approximately 570 nm. In FIG. 5, optical filter 42 transmits the converted light of a wavelength that is approximately 10 nm above and below the wavelength at which converted light intensity is at maximum. Since the reflectivity of optical filter 42 is zero percent, the intensity of light emitted from wavelength converter 40 (light for illumination) for the converted light having a wavelength from approximately 550 nm to approximately 570 nm becomes approximately half. Since the converted light resulting from the wavelength conversion of laser light by wavelength converting component 43 is emitted in all directions, when optical filter 42 completely transmits light of the maximum wavelength and neighboring wavelengths thereof (when reflectivity of optical filter 42 is zero percent), approximately half of the converted light is emitted from wavelength converter 40 as light for illumination. For example, the remaining half of the converted light which is transmitted by optical filter 42 is absorbed by luminaire 5 and does not contribute to the illumination by lighting apparatus 1.

Average color rendering index Ra of lighting apparatus 1 that uses such a wavelength converter 40 was calculated. Here, average color rendering index is an index indicating the magnitude of color variation when test colors (R1 to R8) are illuminated by light of a specimen light source and a reference light. A value of 100 is given when the test color is seen under the reference light, and the value for the test color decreases as the color variation increases. Average color rendering index Ra is expressed as the average of the color rendering indices of the test colors (R1 to R8). Average color rendering index Ra for this embodiment was 80.2.

In this manner, in wavelength converter 40, out of the converted light, converted light of the maximum wavelength and neighboring wavelengths thereof at which light intensity is high was transmitted or absorbed by optical filter 42, thereby making it possible to control the converted light that was emitted from wavelength converter 40. For this reason, in wavelength converter 40 and lighting apparatus 1, by controlling the converted light resulting from the wavelength conversion by wavelength converting component 43 using optical filter 42, the color rendering property of converted light can be improved.

Comparative Example

Figure 6:
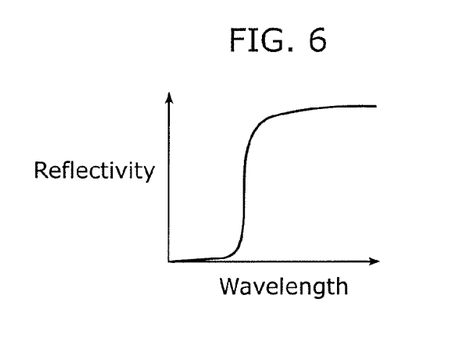
FIG. 6 is a graph illustrating an example of the wavelength and reflectivity of light of an optical filter of a wavelength converter of a lighting apparatus according to a comparative example.

FIG. 6 is a graph illustrating an example of the wavelength and reflectivity of light of an optical filter of a wavelength converter of a lighting apparatus according to a comparative example.

As illustrated in FIG. 6, in the wavelength converter according to the comparative example, the converted light resulting from the wavelength conversion of laser light by the wavelength converting component is completely reflected by the optical filter. Specifically, unlike the above described embodiment, the wavelength converter according to the comparative example does not transmit converted light of the predetermined wavelength included in the wavelength range of the converted light.

Figure 7:
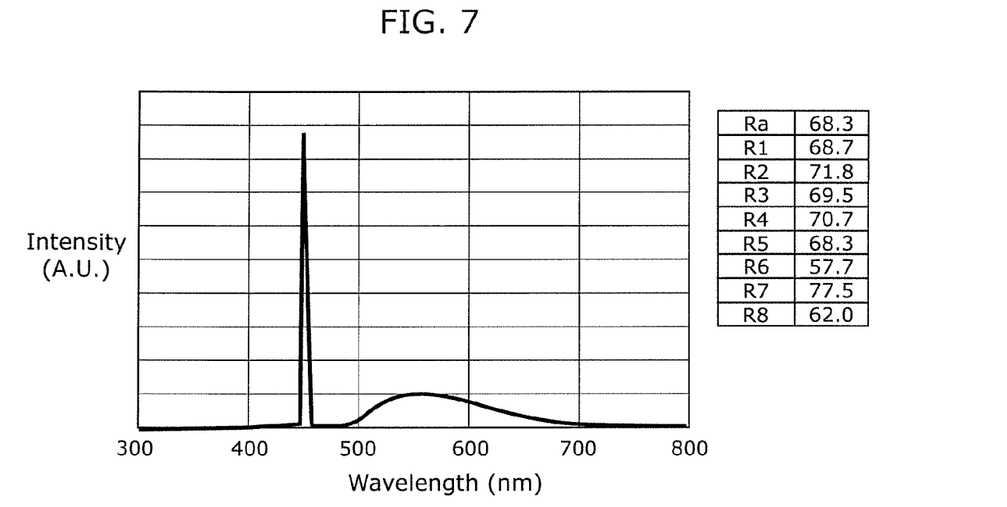
FIG. 7 illustrates a graph showing an example of intensity and wavelength of light emitted from a wavelength converter of a lighting apparatus according to a comparative example, and a table showing an example of an average color rendering index.

FIG. 7 illustrates a graph showing an example of intensity and wavelength of light emitted from a wavelength converter of a lighting apparatus according to a comparative example, and a table showing an example of an average color rendering index.

FIG. 7 illustrates the case where laser light having a peak included in a wavelength range of from approximately 430 nm to approximately 480 nm enters the wavelength converter, when the reflectivity of the optical filter is 100 percent. FIG. 7 illustrates the spectrum of light emitted from the wavelength converter, when a wavelength converter such as that described above is used.

In FIG. 7, the converted light emitted from the wavelength converter is completely reflected by the optical filter. For this reason, in the comparative example, the intensity of the converted light does not decrease, and yellow wavelength converted light that is more intense than that in FIG. 5 of the embodiment is emitted.

Average color rendering index Ra of the lighting apparatus according to the comparative example that uses such a wavelength converter was calculated. Average color rendering index Ra for the comparative example was 68.3. For this reason, the color rendering property and the color reproduction property of light for the lighting apparatus which used the wavelength converter according to the comparative example are poor compared to lighting apparatus 1 which uses wavelength converter 40 according to this embodiment.

Effects

Next, the effects of lighting apparatus 1 which uses wavelength converter 40 according to this embodiment will be described.

As described above, wavelength converter 40 according to this embodiment includes, base 41, wavelength converting component 43 that converts the wavelength of at least part of excitation light (laser light in this embodiment) to emit converted light; and optical filter 42 disposed between base 41 and wavelength converting component 43. Optical filter 42 transmits or absorbs, out of the converted light including a wavelength range of from approximately 470 nm to approximately 750 nm, converted light of a predetermined wavelength included in the wavelength range.

Accordingly, since part of the converted light resulting from the wavelength conversion by wavelength converting component 43 is transmitted or absorbed by optical filter 42, wavelength converter 40 can control the light that is emitted from wavelength converting component 43. Specifically, wavelength converter 40 can cut, out of the converted light which includes a wavelength range of from approximately 470 nm to approximately 750 nm, converted light of a predetermined wavelength which is included in the wavelength range. In this manner, out of the converted light, optical filter 42 transmits or absorbs converted light of the maximum wavelength and neighboring wavelengths thereof at which light intensity is high.

Therefore, wavelength converter 40 can improve color rendering property of light emitted from wavelength converter 40.

Furthermore, lighting apparatus 1 according to this embodiment includes wavelength converter 40 and laser light source 31 which emits excitation light.

Light apparatus 1 also produces the same advantageous effects as described above.

Furthermore, in wavelength converter 40 according to this embodiment, optical filter 42 transmits or absorbs the converted light of the predetermined wavelength that is at most approximately 50 nm above and below a wavelength at which intensity of the converted light is at maximum.

Accordingly, with wavelength converter 40, it is possible to cut the part of the wavelength at which the intensity of converted light is at maximum, and thus the color rendering property of light emitted from wavelength converter 40 can be more reliably improved.

Furthermore, in wavelength converter 40 according to this embodiment, optical filter 42 has a reflectivity of at most approximately 50 percent. Alternatively, optical filter 42 has a rate of absorption of at least approximately 50 percent for the converted light of converted light of the maximum wavelength and neighboring wavelengths thereof.

Accordingly, since wavelength converting component 43 of wavelength converter 40 emits converted light in all directions during wavelength conversion of laser light, approximately half of the converted light emitted enters optical filter 42. Specifically, out of the converted light, wavelength converter 40 can cut at most 50 percent of converted light of the maximum wavelength and neighboring wavelengths thereof at which light intensity is high. For this reason, with wavelength converter 40, the color rendering property of light emitted from wavelength converter 40 can be more reliably improved.

Furthermore, in wavelength converter 40 according to this embodiment, optical filter 42 is in contact with each of base 41 and wavelength converting component 43.

Accordingly, since wavelength converting component 43 is in contact with optical filter 42, the heat generated during the wavelength conversion of laser light by wavelength converting component 43 can be conducted to optical filter 42. Furthermore, optical filter 42 is can conduct this heat to base 41 too. For this reason, in wavelength converter 40, the heat generated in wavelength converting component 43 can be released, and thus the intensity of the converted light resulting from the wavelength conversion by wavelength converting component 43 can be stabilized.

In particular, when base 41 is in contact with heat sink 151, etc., the heat-dissipating effect of wavelength converter 40 can be expected.

In wavelength converter 40 according to this embodiment, optical filter 42 is an optical thin-film comprising a dielectric multilayer film.

This case also produces the same advantageous effects as described above.

Furthermore, in wavelength converter 40 according to this embodiment, base 41 and optical filter 42 are light-transmissive. In addition, the excitation light transmitted by base 41 and optical filter 42 enters wavelength converting component 43.

For example, when laser light is made to enter the surface of the wavelength converting component which is on the side opposite to the optical filter-side, depending on the roughness of the surface of the wavelength converting component, it is difficult to reflect part of the laser light in a desired direction, and it is difficult to control the direction in which laser light is reflected. For this reason, when causing laser light to enter from a surface of the wavelength converting component, and causing converted light to exit from this surface, and causing laser light to be reflected by this surface, it becomes difficult to obtain desired light from the wavelength converting component.

However, in wavelength converter 40 according to this embodiment, laser light enters back face 43b on the optical filter 42-side of wavelength converting component 43, and converted light exits from front face 43a of wavelength converting component 43, and thus, compared to when laser light enters from front face 43a of wavelength converting component 43, it becomes easier to cause part of the laser light to exit in the same direction as converted light, which makes obtaining desired light easier.

Furthermore, in wavelength converter 40 according to this embodiment, the excitation light is blue laser light. In addition, wavelength converting component 43 includes yellow phosphor.

Accordingly, light emitted from wavelength converter 40 includes blue laser light which has passed through wavelength converter 40 without being wavelength-converted and yellow converted light resulting from the wavelength conversion by wavelength converter 40. The light emitted from wavelength converter 40 has had a part of the yellow converted light cut by optical filter 42. For this reason, with wavelength converter 40, the color rendering property of light emitted from wavelength converter 40 can be more reliably improved.

(Other Variations, and so on)

Although the present disclosure is described above based on exemplary embodiments, the present disclosure is not limited to the foregoing exemplary embodiments.

Figure 2B:
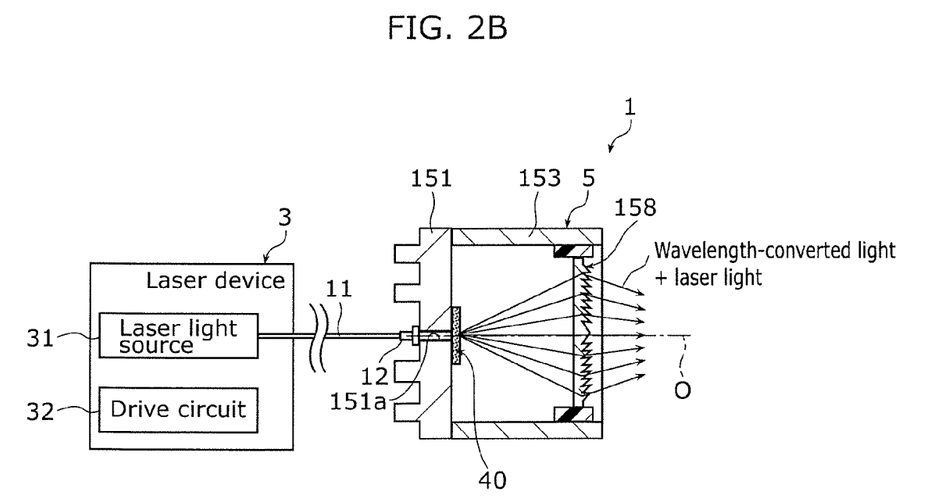
FIG. 2B is a schematic diagram illustrating an example of structural elements according to a variation of the lighting apparatus in FIG. 1A, and shows a cross-sectional view of a luminaire, etc., taken along line II-II in FIG. 1A.

For example, lighting apparatus 1 according to foregoing embodiment includes reflector 157 but need not include reflector 157 as illustrated in FIG. 2B. FIG. 2B is a schematic diagram illustrating an example of structural elements in a variation of the lighting apparatus according to the embodiment described above, and shows a cross-sectional view of the luminaire, etc., taken along line II-II in FIG. 1A. Although reflector 157 reflects the light emitted from wavelength converter 40 toward lens 158 to thereby effectively cause the light emitted from wavelength converter 40 to be irradiated to the outside from the opening of luminaire 5, it does not control the spectrum of light. For this reason, if there is no need to improve the efficiency of lighting apparatus 1, reflector 157 is not an essential element.

Figure 1B:
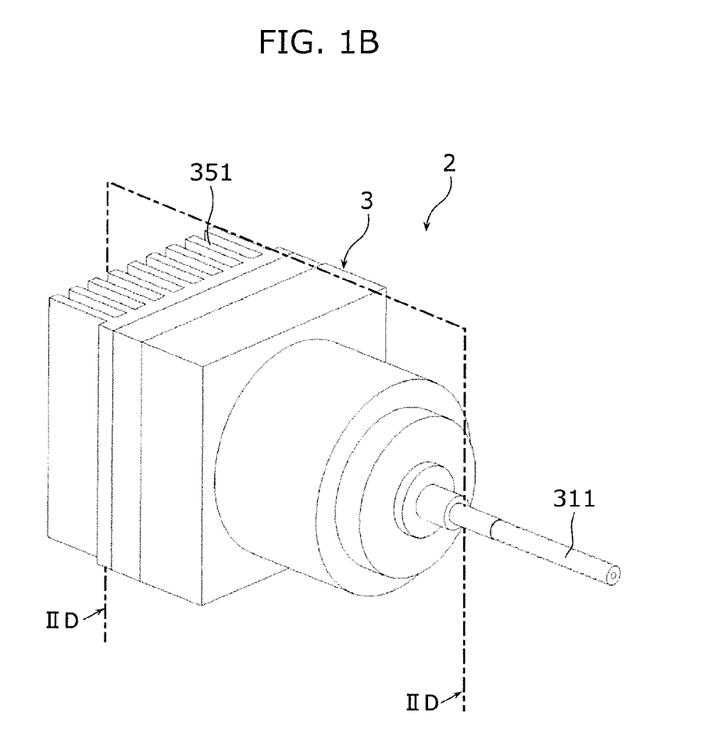
FIG. 1B is a perspective diagram of a lighting apparatus according to a variation.
Figure 2C:
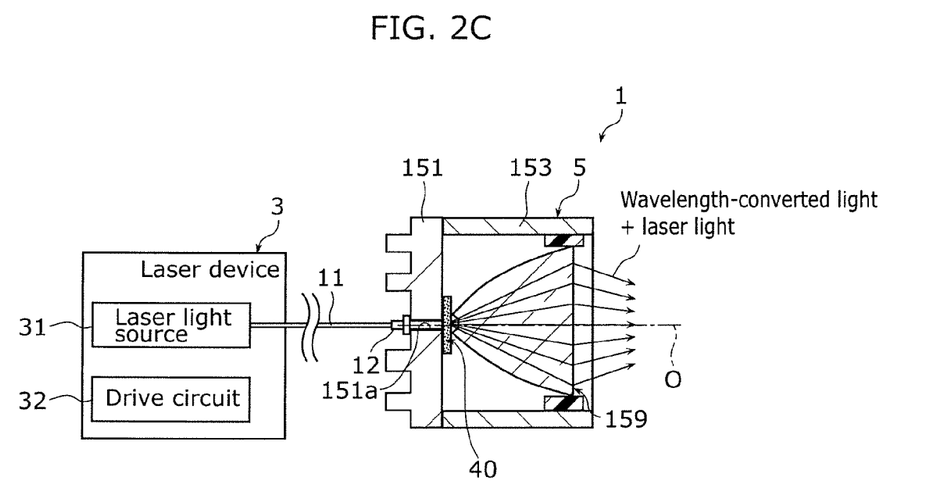
FIG. 2C is a schematic diagram illustrating an example of structural elements according to a variation of the lighting apparatus in FIG. 1A, and shows a cross-sectional view of a luminaire, etc., taken along line II-II in FIG. 1A.

Furthermore, as illustrated in FIG. 2C, lighting apparatus 1 according to the foregoing embodiment may use an irregular-shaped lens 159, without including reflector 157. FIG. 2C is a schematic diagram illustrating an example of structural elements of the lighting apparatus according to a variation of the foregoing embodiment, and shows a cross-sectional view of the luminaire, etc., taken along line IID-IID in FIG. 1B. Irregular-shape lens 159 includes, for example, a flat face along the opening of luminaire 5, a paraboloid face on the sides, and a recess in the shape of a truncated cone, as illustrated in FIG. 2C. Light which enters from the recess of irregular-shaped lens 159 is reflected by the paraboloid face, and emitted toward the direction of the opening of luminaire 5 from the bottom face of the recess. Since the paraboloid face of irregular-shaped lens 159 has the same function as reflector 157, the light emitted from wavelength converting component 43 can be efficiently irradiated to the outside from the opening of luminaire 5 even without reflector 157.

Figure 2D:
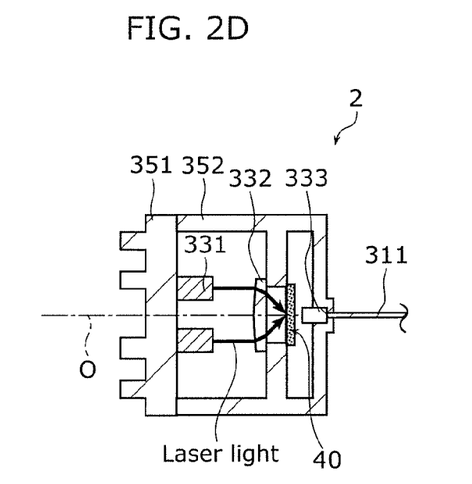
FIG. 2D is a schematic diagram showing an example of structural elements according to a variation of the lighting apparatus in FIG. 1B, and shows a cross-sectional view taken along line IID-IID in FIG. 1B.

Furthermore, as illustrated in FIG. 1B and FIG. 2D, lighting apparatus 2 according to another form is a transmission type lighting apparatus that uses laser light, and includes one or more laser light sources 331, lens 332, wavelength converter 40, light guide 333, optical fiber 311, heat sink 351, exterior portion 352. Lighting apparatus 2 is, for example, used as an endoscope light source or a light source for a microscope. Here, transmission type lighting apparatus 2 which uses laser light is an apparatus in which the back face of wavelength converter 40 is irradiated with laser light, and converted light (fluorescence) resulting from wavelength conversion is emitted from the front face of wavelength converter 40.

As illustrated in FIG. 2D, in lighting apparatus 2 according to another form, the direction of the laser light emitted from one or more laser light sources 331 is changed by lens 332 so that the laser light condenses at and enters wavelength converter 40. The central axis of lens 332 approximately coincides with aforementioned central axis O. Accordingly, it is possible to cause the beams of laser light emitted from laser light sources 331 to condense at wavelength converter 40 and improve light emission luminance of wavelength converter 40.

In this manner, above-described lighting apparatus 2 according to another form further includes lens 332 that is disposed between laser light sources 331 and directs the excitation light emitted by laser light sources 331 to wavelength converter 40, and light guide 333 into which the converted light resulting from the wavelength conversion by wavelength converter 40 enter.

Figure 2E:
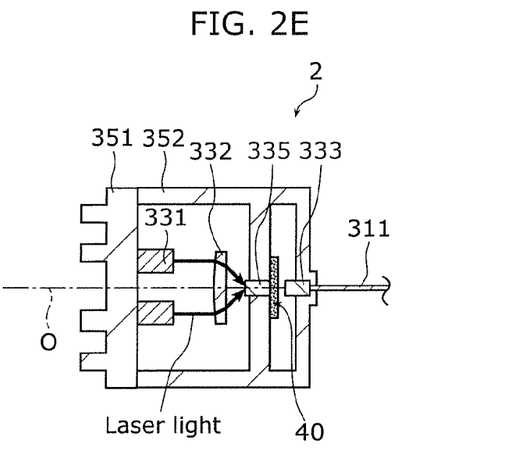
FIG. 2E is a schematic diagram showing an example of structural elements according to a variation of the lighting apparatus in FIG. 1B, and shows a cross-sectional view taken along line IID-IID in FIG. 1B.

Furthermore, as illustrated in FIG. 2E, above-described lighting apparatus 2 according to another form may include light guide 335 disposed between lens 332 and wavelength converter 40. The central axis of light guide 335 approximately coincides with aforementioned central axis O. The cross section of light guide 335 when the transmission path is cut along a plane orthogonal to the direction in which laser light is transmitted is polygonal in shape. Here, the polygonal shape of the cross-section of light guide 335 includes not only a regular polygon but also shapes that can be considered substantially polygonal. In other words, part or all of the faces forming the polygon are not only flat, but may be curved, or wavy faces. It should be noted that the cross-section of light guide 335 may have at least one straight side, and the remaining sides may be arc-shaped. Since the beams of laser light that entered one end of light guide 335 are guided while repeatedly being reflected many times inside light guide 335, the beams of laser light that are guided inside are mixed and exit uniformly from the other end of light guide 335. Accordingly, uniform light enters wavelength converter 40, and thereby light emission evenness of wavelength converter 40 can be improved.

In this manner, above-described lighting apparatus 2 according to another form further includes lens 332 that is disposed between laser light sources 331 and transmits the excitation light emitted by laser light sources 331, and light guide 335 that is disposed between lens 332 and wavelength converter 40 and guides the excitation light transmitted by lens 332 to wavelength converter 40.

Figure 3B:
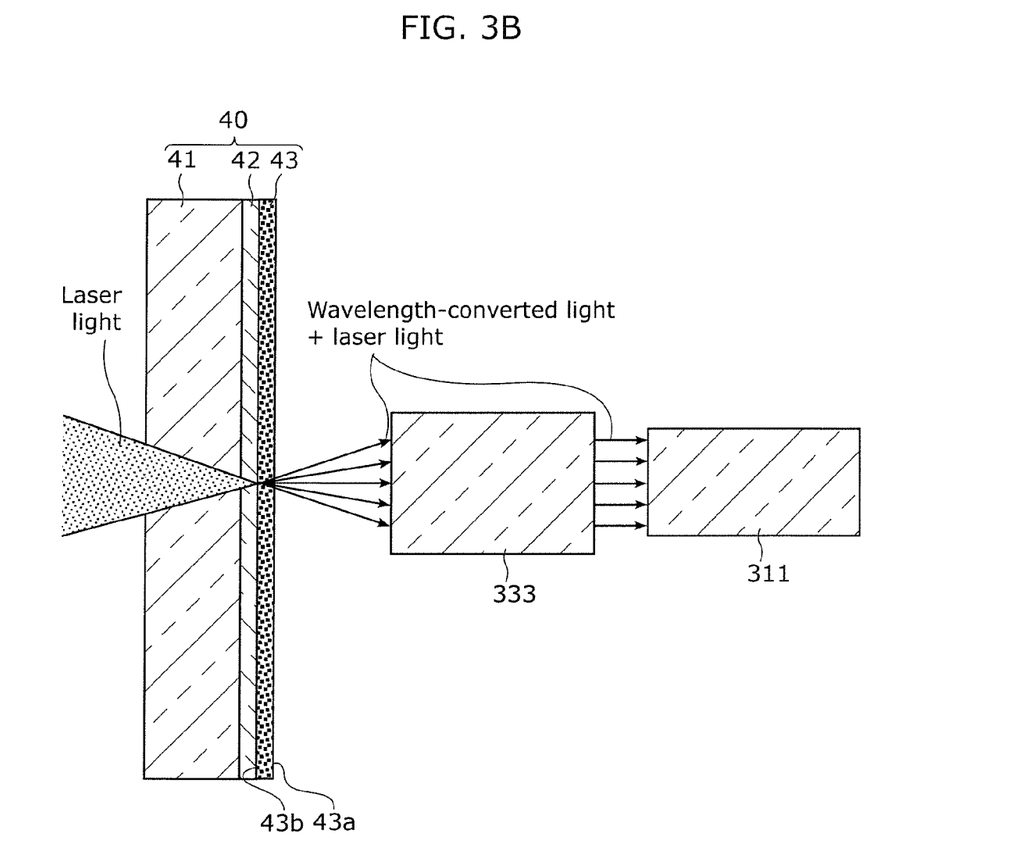
FIG. 3B is an enlarged partial sectional view of an example of a wavelength converter and a light guide of the lighting apparatus in FIG. 1B according to another form.

Furthermore, as illustrated in FIG. 2D and FIG. 3B, the light emitted from wavelength converter 40 enters from one end of light guide 333, is guided inside thereof, and emitted from the other side. The cross section of light guide 333 when the transmission path is cut along a plane orthogonal to the direction in which laser light is transmitted is polygonal in shape. Here, the polygonal shape of the cross-section of light guide 333 includes not only a regular polygon but also shapes that can be considered substantially polygonal. In other words, part or all of the faces forming the polygon are not only flat, but may be curved, or wavy faces. It should be noted that the cross-section of light guide 333 may have at least one straight side, and the remaining sides may be arc-shaped. Since the light emitted from wavelength converter 40 that has entered one end of light guide 333 are guided while repeatedly being reflected many times inside light guide 333, the beams of laser light that are guided inside are mixed and exit uniformly from the other end of light guide 333. The light emitted from the other end of light guide 333 enters one end of optical fiber 311 and are guided. Accordingly, the light emitted from wavelength converter 40 that has been made uniform can enter one end of optical fiber 311, and the light emitted from the other end of optical fiber 311 can illuminate an object uniformly.

In the wavelength converter and light apparatus according to the foregoing embodiment, laser light may enter the surface of the wavelength converter on the side opposite the optical filter-side. For this reason, the wavelength converter and light apparatus according to the foregoing embodiment are not limited to a configuration in which laser light enters the back face of the wavelength converter.

Aside from the above, forms obtained by various modifications to the exemplary embodiment that can be conceived by a person of skill in the art as well as forms realized by arbitrarily combining structural components and functions in the exemplary embodiment which are within the scope of the essence of the present disclosure are included in the present disclosure.

What is claimed is:

1. A wavelength converter, comprising:
a base;
a wavelength converting component that converts a wavelength of at least part of excitation light to emit converted light; and
an optical filter disposed between the base and the wavelength converting component, wherein
the optical filter transmits or absorbs, out of the converted light which includes a wavelength range from 470 nm to 750 nm, converted light of a predetermined wavelength included in the wavelength range, and
the optical filter transmits or absorbs the converted light of the predetermined wavelength that is at most 50 nm above and below a wavelength at which intensity of the converted light is at maximum.

2. The wavelength converter according to claim 1, wherein
the optical filter is in contact with the base and the wavelength converting component.

3. The wavelength converter according to claim 1, wherein
the optical filter is an optical thin-film comprising a dielectric multilayer film.

4. The wavelength converter according to claim 1, wherein
the base and the optical filter are light-transmissive, and
the excitation light transmitted by the base and the optical filter enters the wavelength converting component.

5. The wavelength converter according to claim 1, wherein
the excitation light is blue laser light, and
the wavelength converting component includes yellow phosphor.

6. A wavelength converter, comprising:
a base;
a wavelength converting component that converts a wavelength of at least part of excitation light to emit converted light; and
an optical filter disposed between the base and the wavelength converting component, wherein
the optical filter transmits or absorbs, out of the converted light which includes a wavelength range from 470 nm to 750 nm, converted light of a predetermined wavelength included in the wavelength range, and
the optical filter has a reflectivity of at most 50 percent and a rate of absorption of at least 50 percent for the converted light of the predetermined wavelength.

7. The wavelength converter according to claim 6, wherein
the optical filter is in contact with the base and the wavelength converting component.

8. The wavelength converter according to claim 6, wherein
the optical filter is an optical thin-film comprising a dielectric multilayer film.

9. The wavelength converter according to claim 6, wherein
the base and the optical filter are light-transmissive, and
the excitation light transmitted by the base and the optical filter enters the wavelength converting component.

10. The wavelength converter according to claim 6, wherein
the excitation light is blue laser light, and
the wavelength converting component includes yellow phosphor.

11. A lighting apparatus, comprising:
a wavelength converter, comprising:
a base;
a wavelength converting component that converts a wavelength of at least part of excitation light to emit converted light; and
an optical filter disposed between the base and the wavelength converting component, wherein
the optical filter transmits or absorbs, out of the converted light which includes a wavelength range from 470 nm to 750 nm, converted light of a predetermined wavelength included in the wavelength range;
an excitation light source that emits the excitation light;
a lens that is disposed between the excitation light source and the wavelength converter, and directs the excitation light emitted by the excitation light source, to the wavelength converter; and
a light guide into which the converted light resulting from wavelength conversion by the wavelength converter enters.

12. The lighting apparatus according to claim 11, wherein
the lens transmits the excitation light emitted by the excitation light source; and the light guide is disposed between the lens and the wavelength converter, and guides the excitation light transmitted by the lens, to the wavelength converter.

13. The wavelength converter according to claim 11, wherein the optical filter is in contact with the base and the wavelength converting component.

14. The wavelength converter according to claim 11, wherein the optical filter is an optical thin-film comprising a dielectric multilayer film.

15. The wavelength converter according to claim 11, wherein the base and the optical filter are light-transmissive, and the excitation light transmitted by the base and the optical filter enters the wavelength converting component.

16. The wavelength converter according to claim 11, wherein the excitation light is blue laser light, and the wavelength converting component includes yellow phosphor.

* * * * *